United States Patent [19]

Brown

[11] Patent Number: Plant 7,501

[45] Date of Patent: Apr. 16, 1991

[54] AGLAONEMA PLANT NAMED SUPERBA

[75] Inventor: B. Frank Brown, Palm Bay, Fla.

[73] Assignee: Hartman Plant Laboratories, Inc., Sebring, Fla.

[21] Appl. No.: 375,603

[22] Filed: Jul. 5, 1989

[51] Int. Cl.[5] ..... A01H 5/00
[52] U.S. Cl. ..... Plt./88
[58] Field of Search ..... Plt./88

[56] References Cited

U.S. PATENT DOCUMENTS

P.P. 6,842 6/1989 Brown ..... Plt. 88

*Primary Examiner*—Howard J. Locker
*Attorney, Agent, or Firm*—Foley & Lardner, Schwartz, Jeffery, Schwaab, Mack, Blumenthal & Evans

[57] ABSTRACT

An Aglaonema plant named Superba having white petioles, a green and gray-green striped leaf color and pattern, yellow midribs, relatively large leaves, and an upright, medium tall growth habit.

1 Drawing Sheet

The present invention comprises a new and distinct cultivar of Aglaonema hybrida known by the cultivar name 'Superba'.

The new cultivar is a product of a planned breeding program carried out by the inventor B. Frank Brown in Palm Bay, Fla. The parents of the new cultivar are an unnamed cultivar of *Aglaonema nitidum* 'Curtisii' (seed parent) and an unnamed cultivar of *Aglaonema commutatum* 'Tricolor' (pollen parent). The new cultivar was discovered from the progeny of the stated cross by B. Frank Brown. Asexual propagation by division was used to increase the number of plants for evaluation and has demonstrated the stability of the combination of characteristics of the new cultivar from generation to generation.

The seed parent, 'Curtisii' is characterized by oblanceolate to oblong shaped leaves which are approximately 18 to 46 cm. in ultimate length and approximately 9 to 15 cm. in ultimate width. These ultimate dimensions are both less than corresponding dimensions for 'Superba'. Although the dimensions stated below for 'Superba' are less, they are based on a plant approximately 45–55 weeks old. The petioles of 'Curtisii' are green, as opposed to the essentially white petioles of 'Superba'. A further distinction is that in 'Curtisii' the variegation along the lateral leaf veins is silvery-grey thus resulting in a zebra-like appearance, as opposed to the greyed-green variegation of 'Superba'. A further difference is the slow growth rate of 'Curtisii', which is a contributing factor to the cultivar not being commercial.

The male or parent cultivar 'Tricolor' has an ovate leaf shape similar to 'Superba', but the leaf length (approximately 13–24 cm.) and leaf width (approximately 5–15 cm.) is shorter and narrower, respectively, than a typical leaf of 'Superba'. The petioles of 'Tricolor' are generally the same color as in 'Superba', but the variegation pattern and color differs. The upper surface of the leaves of 'Tricolor' are characterized by pale green blotches along the primary veins. The lower leaf surfaces are mottled cream along the cream colored midrib and the main veins. This differs substantially from the color of the undersurface of the leaves of 'Superba' as described below.

The following observations, measurements and values describe plants of 'Superba' grown in Palm Bay, Fla. under greenhouse conditions which closely approximate those generally used in horticultural practice.

The following traits have been repeatedly observed and are determined to be basic characteristics of 'Superba', which in combination distinguish 'Superba' from other Aglaonema of the same general type.

1. 'Superba' has a different leaf pattern and leaf color than the parent cultivars or other cultivars of these species.
2. 'Superba' has a larger leaf than either of its parents.
3. 'Superba' has white petioles.
4. 'Superba''s combination of yellow midribs and gray stripes is unique.
5. The growth habit is upright and medium tall.

All color references below are measured against The Royal Horticultural Society Colour Chart. Colors are approximate as color depends on horticultural practices such as light level and fertilization rate, among others.

The drawing commprises a front perspective color photograph of a plant of 'Superba', with color being depicted as accurately as possible with illustrations of this type. The photo illustrates a plant of 'Superba' in an eight (8) inch pot approximately 45–55 weeks from a plant obtained by division, grown under appropriate conditions.

Origin: Seedling, *Aglaonema nitidum* 'Curtisii'×*Aglaonema commutatum* 'Tricolor'.

Classification: Aglaonema hybrida cv. 'Superba'.

Propagation: Asexual production either by tissue culture or division.

Plant: In an 8 inch pot after approximately 45 to 55 weeks under appropriate growing conditions from a plantlet obtained by division, 'Superba' will be approximately 25 cm. to 33 cm. from the soil surface to the junction of the petioles of the last two (2) unrolled leaves, and approximately 65 cm. to 75 cm. in width. All measurements are based on the above parameters. The ultimate size of 'Superba' is not known since no plant has as yet reached maturity.

Stem:

*Growth pattern.*—The stem is erect in growth and is approximately 1.9 cm. to 2.5 cm. in diameter five (5) cm. above the soil surface. Internode distance is approximately 1.1 cm. to 1.4 cm. three (3) cm. above the soil.

*Color.*—The stem is 157A in color.

Petiole: The following information is based on the 3rd expanded leaf from the apex.

*Growth pattern.*—The petiole has fleshy edges extending from the midrib that will be referred to as wings. The wings are approximately 4 mm. to 8 mm. wide one (1) cm. below the wing tip. The wings extend from the base of the petiole to within approximately 1.3 cm. to 1.7 cm. of the leaf base. The apex of the wings is emarginate. The petiole follows the stem axis but diverges from the axis approximately 7.0 cm. to 8.0 cm. from the leaf base, forming a horizontal distance from the edge of the stem to the leaf base of approximately 1.5 cm. to 2.5 cm.

*Dimensions.*—The petiole is straight from its base to the base of the leaf. The petiole is approximately 7 mm. to 11 mm. in diameter one-half way between the top of the wing and the base of the leaf.

*Color.*—The petiole wings will be blotched 155B, 159D and 157A, similar to the midrib.

Leaf:

*Growth pattern.*—The leaf is ovate with a cuspidate apex and an obtuse base. The margin is entire. The leaf is asymmetric with the side of the leaf unrolling first having less surface area and fewer undulations on the leaf margin than the side unrolling last. The leaf is oriented nearly parallel to the stem axis at the time of full unrolling, changing to a slightly more horizontal position as more leaves unroll above it. The midrib droops toward the end of the leaf. The leaf blade is straight but angles down slightly from the midrib to the margin.

*Dimensions.*—For the pot size and growing time indicated, the largest leaf is approximately 34 cm. to 39 cm. long and approximately 14 cm. to 16 cm. wide. An average sized leaf is approximately 32 cm. to 36 cm. long and approximately 12 cm. to 15 cm. wide. The leaf is moderately thick.

*Midrib.*—The midrib is thick and prominent.

*Primary veins.*—The primary veins are sunken into the upper surface and protrude out of the under side. The primary veins are the same color as the leaf tissue surrounding them.

*Color and pattern.*—There are numerous areas of the leaf where color is significant, particularly on the upper surface. Upper surface: Main areas of green from margin to midrib: 139A, 136A. Midrib: 154C, 150D. Gray-green stripes: 191D, 198D. Spots: 154C, 150C. Under surface: Main areas of green: 137B. Midrib: yellower than 155B and greener than 159C. Other areas: the striping does not extend through from the upper surface; however, there are areas of 145D surrounding the midrib and randomly toward the margin; primary veins are also 145D.

Axillary breaks: There are approximately 0 to 2 axillary breaks with at least one (1) leaf expanded. Leaves will show color by the 2nd leaf and will have true color and pattern by the 4th leaf.

Inflorescence: Typical of Aglaonema and has no commercial significance. A plant of 'Superba' last bloomed in 1986. At that time the plant was divided and the plants produced from the division have not yet reached flowering maturity. No specific observations were taken when the plant was in bloom in 1986.

Roots: Thick white roots with finer laterals.

General observations: 'Superba' is different from other commercially available Aglaonemas in that it has a different leaf color and pattern than is commercially available on a white petioled Aglaonema. The plant is an upright, medium tall Aglaonema that has a thick textured appearance to the leaves. The combined characteristics make 'Superba' a unique new cultivar.

I claim:

1. A new and distinct cultivar of Aglaonema plant named 'Superba', as described and illustrated.

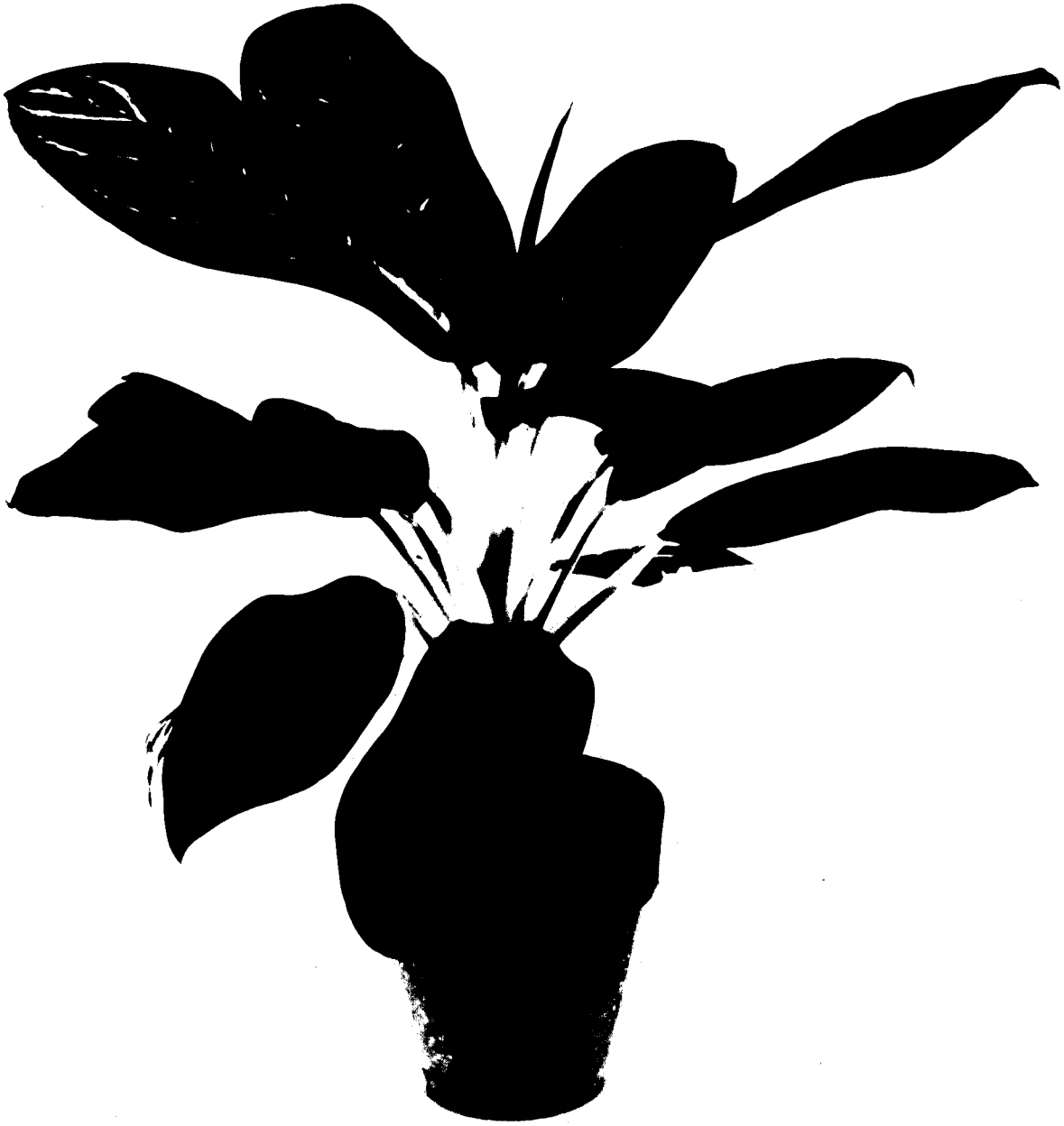

* * * * *